United States Patent [19]

Gainer et al.

[11] Patent Number: 4,629,789
[45] Date of Patent: Dec. 16, 1986

[54] ALKYL SUBSTITUTED PYRIDAZINONES AND PHARMACEUTICAL COMPOSITIONS

[75] Inventors: James Gainer, Worsley, England; Richard Göschke, Bottmingen, Switzerland

[73] Assignee: Ciba-Geigy Corporation, Ardsley, N.Y.

[21] Appl. No.: 789,995

[22] Filed: Oct. 22, 1985

[30] Foreign Application Priority Data

Oct. 23, 1984 [GB] United Kingdom ............ 8426804

[51] Int. Cl.$^4$ .......................................... C07D 413/10
[52] U.S. Cl. .................................................. 544/114
[58] Field of Search ............... 544/114; 514/234, 237, 514/238, 240

[56] References Cited

U.S. PATENT DOCUMENTS 3,975,388  8/1976  Hakim et al. ................... 544/114

FOREIGN PATENT DOCUMENTS 1488330  10/1977  United Kingdom .

OTHER PUBLICATIONS

Curran et al., *Chemical Abstracts*, vol. 77 (1972) No. 19664f, Substance Index, vol. 77 (1922), p. 3370CS.

Albright et al., *Chemical Abstracts*, vol. 90 (1979), No. 38855d, Substance Index, vol. 90 (1979), p. 5069CS.

*Primary Examiner*—Robert W. Ramsuer
*Attorney, Agent, or Firm*—Michael W. Glynn; Irving M. Fishman

[57] ABSTRACT

The present invention relates to novel 6-phenyl-5-alkyl substituted-4,5-dihydro-3(2H)-pyridazinones of formula I:

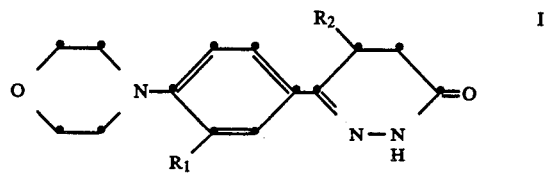

in which $R_1$ is halogen, lower alkyl, lower alkoxy, $NO_2$, $NH_2$, $NHCOR_3$ ($R_3$ is H or $C_1$-$C_4$ alkyl), CN, carboxy, lower alkoxycarbonyl, carbamoyl, $CF_3$, or OH and $R_2$ is $C_1$-$C_4$ alkyl; the tautomeric forms and salts thereof; as their racemic mixtures or as the individual optically-active forms.

Compounds (I) are useful in pharmaceutical preparations having improved antithrombotic activity.

5 Claims, No Drawings

ALKYL SUBSTITUTED PYRIDAZINONES AND PHARMACEUTICAL COMPOSITIONS

The present invention relates to 6-phenyl-5-alkylsubstituted-4,5-dihydro-3-(2H)-pyridazinones, processes for producing them, to pharmaceutical preparations containing these compounds, and to their use.

In German Offenlegungsschrift No. 2,207,517 there are described, inter alia, 6-phenyl-4,5-dihydro-3(2H)-pyridazinones which are substituted in the p-position of the phenyl group by a heterocycle and which exhibit antihypertensive activity.

Moreover, in GB Patent Specification No. 2094302A there are disclosed and claimed 4,5-dihydro-3-(2H)-pyridazinones having antithrombotic activity and having the formula

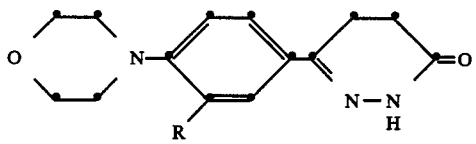

in which R is a halogen atom, or the amino, acetylamino, methyl, cyano, hydroxyl, methoxy or trifluoromethyl group, and the tautomeric forms and salts thereof.

Surprisingly, we have now found that compounds having markedly superior antithrombotic activity are those having the formula I:

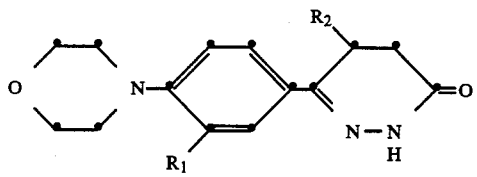

in which $R_1$ is halogen, lower alkyl, lower alkoxy, nitro, amino, $NHCOR_3$ (in which $R_3$ is hydrogen or $C_1$-$C_4$, preferably $C_1$-$C_2$ alkyl, $R_3$ preferably being hydrogen), cyano, carboxy, lower alkoxycarbonyl, carbamoyl, trifluoromethyl, or hydroxy; and $R_2$ is $C_1$-$C_4$ alkyl; the tautomeric forms and acid addition salts thereof; as their racemic mixtures or as the individual optically-active forms.

In the present specification and claims, the term "lower" denotes residues having at most 4, more preferably 1 or 2 carbon atoms.

$R_1$ as lower alkyl is e.g. ethyl, propyl, isopropyl, butyl, isobutyl or t-butyl and especially methyl;

$R_1$ as lower alkoxy is e.g. ethoxy, propoxy, isopropoxy, butoxy, isobutoxy and, especially methoxy; and $R_1$ as lower alkoxycarbonyl is e.g. methoxycarbonyl or ethoxycarbonyl.

Halogen atoms $R_1$ may be fluorine or iodine but are preferably chlorine or bromine atoms.

Preferred compounds of formula I are those wherein $R_2$ is methyl or ethyl, especially methyl and $R_1$ has the meaning as given above and the tautomeric forms, acid addition salts and optical isomers thereof. Of particular interest in this invention are compounds of formula I wherein $R_1$ is amino, $NHCOR_3$ (wherein $R_3$ is hydrogen or $C_1$-$C_4$, preferably $C_1$-$C_2$ alkyl, especially hydrogen) cyano or trifluoromethyl and $R_2$ is methyl and the tautomeric forms, acid addition salts and optical isomers thereof.

Of very particular interest are compounds of formula I, wherein $R_1$ is $NHCOR_3$ (wherein $R_3$ is hydrogen or $C_1$-$C_2$ alkyl) or cyano and $R_2$ is methyl and tautomeric forms and optical isomers thereof.

Of most particular interest is a compound of formula I, wherein $R_1$ is cyano and $R_2$ is methyl and tautomeric and optical isomers thereof.

The compounds of the formula I which are described in the Example subsequently given are to be mentioned in particular.

Compounds of formula I according to the present invention may be prepared by methods which are known per se, and, if desired, separated into individual optical isomers using e.g. optically active acids such as (+) or (−) tartaric acid or D+ camphor sulfonic acid. Alternatively they may be prepared using optically active intermediates.

The compounds of formula I can be obtained, for example by reacting a ketocarboxylic acid of formula II:

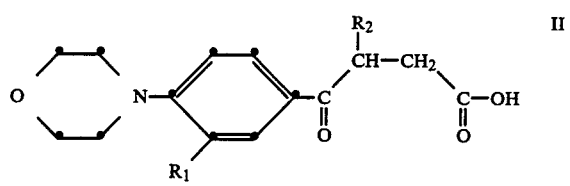

in which $R_1$ and $R_2$ have their previous significance, or a reactive derivative of such a ketocarboxylic acid, with hydrazine. The hydrazine used is conveniently in hydrate form which, when used in excess, can also serve as reaction solvent. It is more advantageous, however, to add an additional solvent. Suitable inert solvents are alcohols e.g. methanol, ethanol, isopropanol, n-butanol, isoamyl alcohol, glycols and glycol ethers e.g. ethylene glycol, diethylene glycol, ethylene glycol monomethyl ether (methyl glycol) or ethylene glycol monoethyl ether (ethyl glycol); or ethers, especially water-soluble ethers, such as tetrahydrofuran, dioxane or ethylene glycol dimethyl ether (diglymes); or water; or mixtures of these solvents, especially mixtures with water, e.g. aqueous ethanol. The reaction temperatures are advantageously between 20° and 200° C., usually between 60° usually between 60° and and 80° C.

Suitable reactive derivatives of acids II are e.g. the esters, in particular $C_1$-$C_6$ alkyl esters such as methyl or ethyl esters; or nitriles having the formula III, as hereinafter defined. Other reactive derivatives are the acid amides and acid halides of the acids of formula II, especially the acid chlorides or acid bromides. Further suitable reactive derivatives of acids II can be formed in situ during the reaction. These include e.g. hydrazones of formula $R_4-C(=N-NH_2)-CH(R_2)-CH_2COOH$, hydrazides of formula $R_4-CO-CH(R_2)-CH_2-CONHNH_2$ and the hydrazones of the hydrazides of formula $R_4-C(=N-NH_2)-CH(R_2)-CH_2CONHNH_2$ in which $R_4$ is a radical of formula:

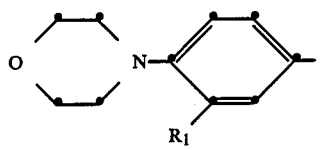

The starting materials formed in situ are produced from acids II and are reacted directly to give compounds of formula I rather than being isolated from the reaction mixture.

Compounds of formula II in which $R_1$ and $R_2$ have their previous signifcance are known compounds and can be prepared from a benzaldehyde derivative of formula VI, according to the following scheme:

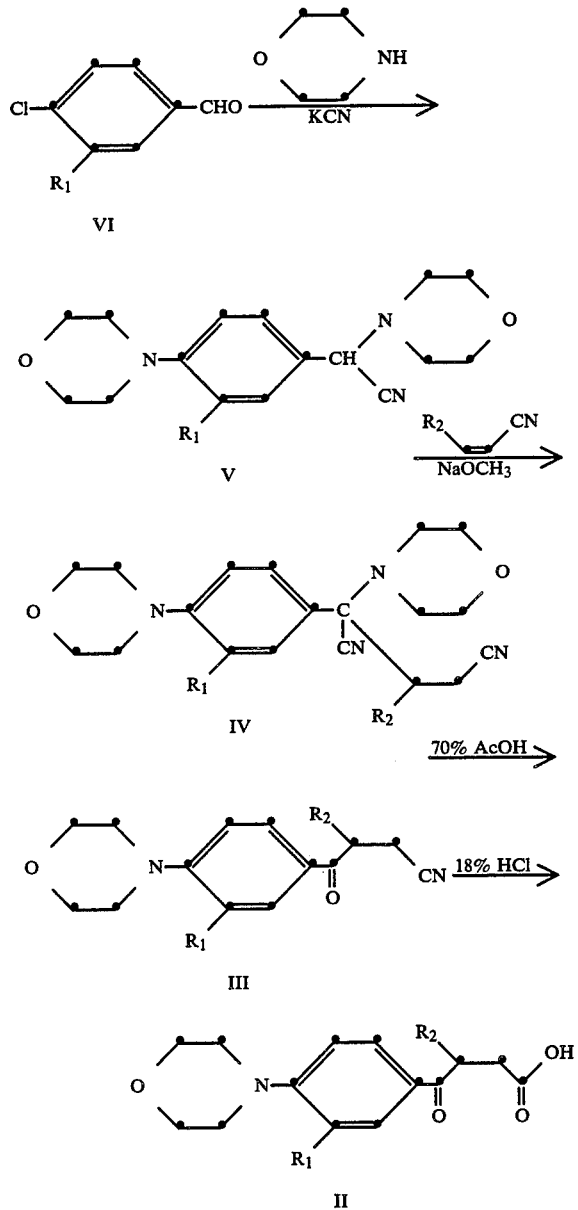

Furthermore, compounds of formula I can be obtained by reacting compounds of formula VII:

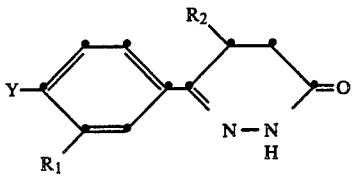

in which $R_1$ and $R_2$ have their previous significance and Y is a detachable group together with hydrogen, e.g. halogen or thioalkyl, with morpholine, in the manner described e.g. in GB No. 2094302A.

Compounds of formula I may also be produced by reacting a compound of formula VIII:

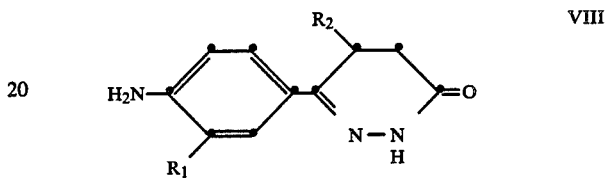

in which $R_1$ and $R_2$ have their previous significance, with a diethyl derivatives of formula IX:

in which Y has its previous significance and is preferably halogen, especially chlorine or bromine, e.g. in the manner described in GB No. 2094302A.

Within the limits of the definition of the final products, substituents can be introduced, modified or detached in the compounds of the formula I obtained.

Compounds of formula I in which $R_1$ is amino can be obtained, for example, by selectively reducing the nitro group to an amino group in a compound of formula X:

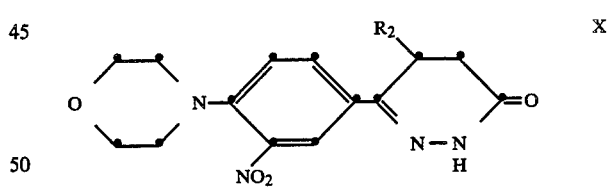

wherein $R_2$ has its previous significance. The reduction technique used is that described in GB No. 2094302A.

The amino compounds of formula I thus obtained, may be converted, in turn, into compounds of formula I in which $R_1$ is acylamino, cyano or chloro by applying established amino conversion techniques. For example, compounds of formula I wherein $R_1$ is a free amino group can be converted by means of an acylating agent e.g. an acetyl halide or acetic anhydride, into compounds of formula I wherein $R_1$ is an acylamino group. Acylation is preferably effected in the presence of an organic base e.g. pyridine, or of a tertiary alkylamine e.g. triethylamine or N-ethyldiisopropylamine.

Resulting compounds of formula I, in which $R_1$ is an amino group can be converted into an acylamino group as defined, as for example into an $NHCOR_3$, wherein $R_3$ is as defined under formula I, by using e.g. procedures described in GB No. 2094302 A.

Compounds of formula I wherein $R_1$ is a halogen atom or the cyano group can be produced by heating a compound of formula XI:

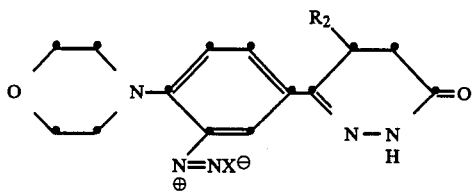

wherein $X^\ominus$ is an anion of a mineral acid, e.g. in the pesence of copper or a cuprous salt e.g. a halide or cyanide. An anion of a mineral acid is e.g. an anion of a hydrohalic acid. When the group introduced is fluorine, $X^\ominus$ is a fluoride or tetrafluoroborate anion. When $X^\ominus$ in formula XI is a fluoride or tetrafluoroborate anion, the heating of compound XI is performed in hydrofluoric acid or in tetrafluoroboric acid. To introduce a cyano group R, the diazonium salt XI is reacted, for example, with cuprous cyanide which is present as a complex with KCN in solution. A diazonium salt XI is reacted e.g. with a mixture of KCN and cuprous sulfate. The diazonium salt is cleaved thermally at temperatures between 30° and 150° C., conveniently between 30° and 40° C. when a diazonium fluoride is present and between 100° and 150° C. when a diazonium tetrafluoroborate is present.

The diazotisation of aromatic amines is performed, for instance, with an alkali metal nitrite e.g. sodium nitrite, especially anhydrous sodium nitrite. Diazotisation is effected e.g. at between $-10°$ and $+10°$ C., conveniently between 0° and 5° C. By reaction with a mineral acid, compounds of formula XI are obtained in which $X^\ominus$ is an anion of a mineral acid.

Compounds of formula I in which $R_1$ is a halogen atom can be produced, for instance, by halogenating compounds of formula XII:

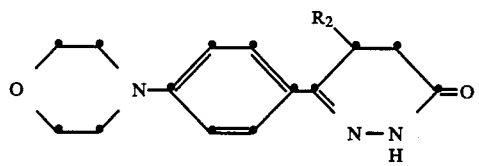

in which $R_2$ previous significance, using, e.g. the procedure described in GB No. 2094302A.

Compounds of formula I in which $R_1$ is a free hydroxyl group or an amino group can be obtained by solvolysing or hydrogenolysing a compound of formula XIII:

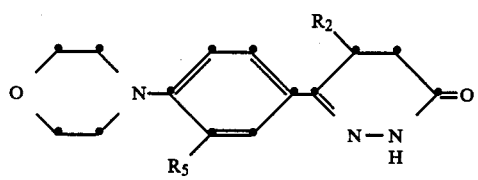

wherein $R_2$ has its previous significance and $R_5$ is a readily solvolysable or hydrogenolysable ether group or acyloxy group, or an amino group protected by a suitable protective group e.g. a tertiarybutoxycarbonyl group, using e.g. the procedures described in GB No. 2094302A.

Furthermore, compounds of the formula I in which $R_1$ is a hydroxyl group can be converted, in a manner known per se, by transesterification or by etherification, into compounds of the formula I wherein $R_1$ is a halogen atom or a methoxy group.

The methods described can be performed, in a customary manner, at room temperature, with cooling or heating, under normal or elevated pressure and, if necessary, in the presence or absence of a diluent, catalyst or condensation agent. The reactions can, if required, also be carried out in an inert-gas atmosphere, for example in that of nitrogen.

The novel intermediates of type III and IV, wherein $R_1$ and $R_2$ have their previous significance, were prepared using modified procedures described by J. D. Albright et al, J. Med. Chem. 15; 881 (1978).

The compounds of the formula (I) have valuable pharmacological properties. For instance they inhibit selectively Type F III human platelet cyclic AMP phosphodiesterase at concentrations in the range $10^{-4}$ to $10^{-10}$ molar. When tested by a modification of the method of Micketa and Asanot (Biochim. Biophys. Acta 429 485–497 (1976) they thus exhibit for example a pronounced antithrombotic action. This can be demonstrated for example in the guinea pig by virtue of the suppression of thrombocytopenia after induction by means of ADP [Artery 8(5): 457–469 (1980] in the dose range of about 30 to 300 mg/kg p.o., and on the basis of the suppression of the thrombosis forming on a cotton thread in an extracorporeal shunt in the rat (method analogous to Brit. J. Pharmacol., 77, 029 (1983) in the dose range of about 0.1 to 50 mg/kg p.o., as well as by virtue of the suppression of the platelet aggregation. The compounds of the general formula I are accordingly suitable in particular for the treatment of thrombotic diseases, and can be used as active ingredients in antithrombotic pharmaceutical prepartions.

Compounds of formula (I) als reduce arterial blood pressure and have positive inotropic properties. They are suitable therefore for treatment of hypertension or heart failure.

The present invention also includes the intermediate compounds having the formulae III, and IV as hereinbefore defined.

Also embraced by the invention are therapeutic compositions comprising an antithrombotically active proportion of a compound of the formula I together with a pharmaceutically acceptable solid carrier or liquid diluent.

A compound of the formula I wherein $R_1$ is an amino group can, if desired, be converted into an acid addition salt in a manner known per se. Of particular use for producing acid addition salts are those acids which are suitable for the formation of therapeutically applicable salts. The following may be mentioned as examples of suitable acids: hydrohalic acids, sulfuric acids, phosphoric acids, nitric acid, perchloric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, or pyruvic acid; phenylacetic acid, benzoic acid, p-aminobenzoic acid, anthranilic acid, p-hydroxybenzoic acid, salicyclic acid or p-aminosalicyclic acid, embonic acid, methanesulfonic acid, ethanesulfonic acid, hydroxyethanesulfonic acid or ethylenesulfonic acid; halogenobenzenesulfonic acid, toluenesulfonic acid, naphthalenesulfonic acid or sulfanilic acid; and methionine, trypthophane, lysine or arginine.

Depending on the process conditions, the compound of the formula I wherein $R_1$ is an amino group can be prepared directly as an acid addition salt.

The acid addition salts of the novel compounds can be converted, in a manner known per se, into the free compound, for example with basic agents, such as alkalies or ion exchangers. On the other hand, the free bases obtained can form salts with organic or inorganic acids.

The pharmaceutical preparations according to the invention contain at least one compound of the formula I as active ingredient, together with a customary pharmaceutical carrier. The nature of the carriers used is governed largely by the field of application. The pharmaceutical compositions according to the invention, which contain compounds of the formula I as active ingredients, can be administered orally, parenterally or rectally.

Suitable for oral treatment of thrombosis are, in particular, solid dosage units, such as tablets, dragees and capsules, which preferably contain between 10 and 90% of an active substance of the general formula I in order to render possible the administration of daily doses of between 0.01 and 100 mg/kg, preferably between 0.1 and 10 mg/kg, particularly between 0.1 and 5 mg/kg, to warm-blooded animals having a body weight of about 70 kg. Tablets and dragee cores are produced by combining the compounds of the formula I with solid pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycols of suitable molecular weight. Dragee cores are subsequently coated for example with concentrated sugar solutions which can also contain for example gum arabic, talcum and/or titanium dioxide, or with a lacquer dissolved in readily volatile organic solvents or solvent mixtures. Colouring agents may be added to these coating, for example for identification of the various dosage amounts. Soft gelatine capsules and other closed capsules consist for example of a mixture of gelatine and glycerin, and can contain for example mixtures of a compound of the formula I with polyethylene glycol. Hard gelatine capsules contain for example granulates of an active substance with solid pulverulent carriers, such as lactose, saccharose, sorbitol or mannitol; starches, such as potato starch, maize starch or amylopectin, cellulose derivatives as well as magnesium stearate or stearic acid.

Suitable dosage units for rectal administration are for example suppositories which consist of a combination of an active substance with a suppository foundation substance based on natural or synthetic triglycerides (for example cocoa butter), polyethylene glycols or suitable higher fatty alcohols; and gelatine retal capsules which contain a combination of the active substance with polyethylene glycols.

For liquids to be taken orally, such as syrups and elixiers, the concentration of active substance is chosen to ensure that a single dose can be easily measured out, for example as the content of a tea-spoon or of a measuring spoon, for example 5 ml, or as a multiple of these amounts.

The following Examples a) to e) are intended to illustrate some typical forms of application, but in no way do they represent the only embodiments thereof.

(a) 100.0 g of active substance are mixed with 610.0 g of lactose and 442.0 g of potato starch; the mixture is then moistened with an alcoholic solution of 8 g of gelatine, and is granulated through a sieve. The granulate is dried, and 60.0 g of talcum, 10.0 g of magnesium stearate and 20.0 g of colloidal silicon dioxide are mixed in; and the mixture is subsequently pressed to form 10,000 tablets, each weighing 125 mg and each containing 10 mg of active substance. The tablets can, if desired, be provided with grooves for a more precise adjustment of the dosage amount.

(b) A granulate is prepared from 100.0 g of active substance, 379 g of lactose and the alcohlic solution of 6.0 g of gelatine; after drying, the granulate is mixed with 10.0 g of colloidal silicon dioxide, 40.0 g of talcum, 60.0 g or potato starch and 5.0 g of magnesium stearate, and the mixture is pressed out to form 10,000 dragee cores. These are subsequently coated with a concentrated syrup prepared from 533.5 g of crystallised saccharose, 20.0 g of shellack, 75.0 g of gum arabic, 250.0 g of talcum, 20.0 g of colloidal silicon dioxide and 1.5 g of colouring agent, and finally dried. The dragees obtained each weigh 150 mg and each contain 10 mg of active substance.C (c) 10.0 g of active substance and 1990 g of finely ground suppository foundation substance (for example cocoa butter) are thoroughly mixed and then melted. The melt is maintained homogeneous by stirring whilst 1000 2.0 g suppositories each containing 25 mg of active substance are being poured.

(d) To prepare a syrup having a content of active substance of 0.25% there are dissolved in 3 litres of distilled water 1.5 litres of glycerin, 42 g of p-hydroxybenzoic acid methyl ester, 18 g of p-hydroxybenzoic acid-n-propyl ester and, with slight warming, 25.0 g of active substance; to this solution are then added 4 litres of 70% sorbitol solution, 1000 g of crystallised saccharose, 350 g of glucose and an aroma substance, for example 250 g of "Orange Peel Soluble Fluid", Eli Lilly and Co., Indianapolis, or 5 g of natural lemon aroma and 5 g of "half and half" essence, both from Haarmann and Reimer, Holzminden, Germany; the solution obtained is filtered, and the filtrate is subsequently made up with distilled water to 10 litres.

(e) To prepare a drip solution containing 1.5% of active substance, 150.0 g of active substance and 30 g of sodium cyclamate are dissolved in a mixture of 4 litres of ethanol (96%) and 1 litre of propylene glycol. A mixture of 3.5 litres of 70% sorbitol solution and 1 litre of water is prepared separately and is then added to the above solution of active substance. An aroma substance, for example 5 g of cough-sweet aroma of 30 g of grapefruit essence, both from Haarmann and Reimer, Holzminden, Germany, is added; the whole is well mixed, filtered and made up with distilled water to 10 litres.

The examples which follow further illustrate the production of the novel compounds of the formula I, but in no way do they limit the scope of the invention. The temperature values are in degrees Centigrade. Parts given in the Examples are given by weight if not otherwise mentioned, as for example parts by volume.

EXAMPLE 1

6-(4-morpholino-3-nitrophenyl)-4,5-dihydro-5-methyl-3(2H)-pyridazinone (i) 4-(4-Morpholino-3-nitrophenyl)-4-(cyano)-4-(morpholino)-3-methylbutyronitrile A solution of 8.0 parts of crotononitrile in 20 parts by volume of tetrahydrofuran is added to a stirred mixture of 16.5 parts of α-morpholino-α(4-morpholino-3-nitrophenyl)-acetonitrile in 150 parts by volume of tetrahydrofuran and 1.5 parts of potassium hydroxide in 5 parts by volume of methanol at room temperature under an atmosphere of nitrogen. The reaction mixture is stirred for a further 6 hours, diluted with 500 parts by volume of water and extracted with 4×250 parts by volume of ethyl acetate. The combined organic extracts are dried over magnesium sulphate and concentrated under vacuum. The resulting crude product is triturated with a mixture of 50 parts by volume of ethyl acetate and hexane. The solid product is collected, washed with ethyl acetate and dried at 80° under vacuum to give 4-(4-morpholino-3-nitrophenyl)-4-(cyano)-4-(morpholino)-3-methylbutyronitrile having melting point 175°–177° C.

H'NMR ppm (DMSOd$_6$): 7.9, 1H, d (J=2 Hz); 7.7, 1H, dd (J=8 Hz; 2 Hz); 7.4, 1H, d (J=8 Hz); 3.7, 8H, m; 3.1, 4H, m; 2.7, 2H, m; 2.4, 4H, m; 2.2, 1H, m; 0.9, 3H, d (J=7 Hz).

(ii) 4(4-Morpholino-3-nitrophenyl)-4-oxo-3-methylbutyronitrile. A mixture of 10.1 parts of 4(4-morpholino-3-nitrophenyl)-4-cyano-4-morpholino-3-methylbutyronitrile in 70 parts by volume of glacial acetic acid together with 8 parts by volume of water is heated on a steam bath for 18 hours. The reaction mixture is concentrated under vacuum and the residual oil is dissolved in 200 parts of volume of dichloromethane and washed with 3×100 parts by volume of brine, 3×100 parts by volume of water, dried over magnesium sulphate, filtered and concentrated under vacuum to give 4(4-morpholino-3-nitrophenyl)-4-oxo-3-methylbutyronitrile.

H'NMR ppm (DMSOd$_6$): 8.5, 1H, d (J=2 Hz); 8.1, 1H, dd (J=8 Hz, 2 Hz); 7.2, 1H, d (J=8 Hz); 3.9, 5H, m; 3.3, 4H, m; 2.7, 2H, d (J=6 Hz); 1.4, 3H, d (J=7 Hz).

(iii) 4(4-Morpholino-3-nitrophenyl)-4-oxo-3-methylbutanoic acid. A mixture of 7.3 parts of 4(4-morpholino-3-nitrophenyl)-4-oxo-3-methylbutyronitrile in 120 parts by volume of 18% hydrochloric acid is heated at 100° C. for 1 and half hours. The reaction mixture is diluted with 500 parts by volume of water and extracted with 3×200 parts by volume of ethyl acetate. The combined organic extract is washed with 3×100 parts by volume of brine, 3×100 parts by volume of water, dried over magnesium sulphate, charcoal treated, filtered and concentrated under vacuum to give 4(4-morpholino-3-nitrophenyl)-4-oxo-3-methylbutanoic acid having melting point 127°–129° C. Recrystallisation from aqueous ethanol raised the melting point to 129°–131° C.

Calculated for C$_{15}$H$_{18}$N$_2$O$_6$: %C 55.89; %H 5.63; %N 8.69; Found: %C 55.77, %H 5.48; %N 8.74

(iv) 6-(4-Morpholino-3-nitrophenyl)-4,5-dihydro-5-methyl-3(2H)-pyridazinone. A mixture of 12.2 parts of 4(4-morpholino-3-nitrophenyl)-4-oxo-3-methylbutanoic acid, 3.8 parts of hydrazine hydrate in 50 parts by volume of absolute ethanol is heated at reflux for 4 hours, cooled and filtered. The solid product is collected, washed with hexane and dried at 80° C. under vacuum to give 6-(4-morpholino-3-nitrophenyl)-4,5-dihydro-5-methyl-3(2H)pyridazinone melting at 223°–225° C. Recrystallisation from a mixture of ethanol and dimethylformamide raises the melting point to 225°–227° C.

Calculated for C$_{15}$H$_{18}$N$_4$O$_4$: %C 56.59; %H 5.70; %N 17.60; Found: %C 56.52; %H 5.42; %N 17.69

EXAMPLE 2

6-(3-Aminophenyl-4-morpholino)-4,5-dihydro-5-methyl-3(2H)-pyridazinone 8.2 parts of 6-(4-morpholino-3-nitrophenyl)-4,5-dihydro-5-methyl3(2H)-pyridazinone and 1 part of 5% palladium on charcoal in 400 parts by volume of dimethylformamide is hydrogenated at room temperature and 2.6 bar pressure. The reaction mixture is filtered and the filtrate is concentrated to dryness. The solid residue is triturated with ethyl acetate, filtered, washed with hexane and dried at 80° C. under vacuum to give 6-(3-aminophenyl-4-morpholino)-4,5-dihydro-5-methyl-3(2H)-pyridazinone melting at 201°–203° C. Recrystallisation from a mixture of ethanol and dimethylformamide raises the melting point to 204°–207° C.

Calculated for C$_{15}$H$_{20}$N$_4$O$_2$: %C 62.48; %H 6.99; %N 19.43 Found: %C 62.05; %H 7.09; %N 19.40

EXAMPLE 3

6-(3-acetamidophenyl-4-morpholino)-4,5-dihydro-5-methyl-3(2H)-pyridazinone

A mixture of 2.0 parts of 6-(3-aminophenyl-4-morpholino)-4,5-dihydro-5-methyl-3(2H)-pyridazinone, 0.9 parts of NN-diisopropylethylamine and 0.8 parts of acetic anhydride in 60 parts by volume of dimethylformamide is stirred at room temperature for 26 hours. The reaction mixture is concentrated under vacuum and the solid residue is collected, washed with 40°–60° petroleum ether and dried at 80° under vacuum to give 6-(3-acetamidophenyl-4-morpholino)-4,5-dihydro-5-methyl-3(2H)-pyridazinone melting at 226°–228° C. Recrystallisation from absolute ethanol raises the melting point to 228°–230° C.

Calculated for C$_{17}$H$_{22}$N$_4$O$_3$: %C 61.80; %H 6.71; %N 16.96 Found: %C 61.88; %H 6.61; %N 16.92

EXAMPLE 4

6-(4-Morpholino-3-propionylaminophenyl)-4,5-dihydro-5-methyl-3(2H)-pyridazinone The title compound was prepared using propionic anhydride by the procedure described in Example 3 and has melting point 193°–196° C. Recrystallisation from absolute ethanol raises the melting point to 198°–201° C.

Calculated for C$_{18}$H$_{24}$N$_4$O$_3$: %C 62.77; %H 7.02; %N 16.27 Found: %C 62.54; %H 7.13; %N 16.17

EXAMPLE 5

6-(3-Formylaminophenyl-4-morpholino)-4,5-dihydro-5-methyl-3(2H)-pyridazinone 0.5 parts of 6-(3-aminophenyl-4-morpholino)-4,5-dihydro-5-methyl-3(2H)-pyridazinone in 5 parts by volume of formic acid are heated at reflux for 30 minutes, cooled and diluted with 10 parts by volume of water. The solid product is collected, washed with water, diethyl ether and dried at 40° C. under vacuum to give 6-(3-formylamino-phenyl-4-morpholino)-4,5-dihydro-5-methyl-3(2)-pyridazinone and has melting point 192°–194° C. Recrystallisation from absolute ethanol raises the melting point to 196°–198° C.

Calculated for C$_{16}$H$_{20}$N$_4$O$_3$: %C 60.74; %H 6.37; %N 17.71; Found: %C 60.49; %H 6.37; %N 17.54

EXAMPLE 6

6-(3-Chlorophenyl-4-morpholino)-4,5-dihydro-5-methyl-3(2H)-pyridazinone 1.2 parts of 6-(3-aminophenyl-4-morpholino)-4,5-dihydro-5-methyl-3(2H)-pyridazinone in 10 parts by volume of concentrated hydrochloric acid and 10 parts by volume of water is diazotised at 0°–5° C. with a solution of 0.4 parts of sodium nitrite in 5 parts by volume of water. After 15 minutes, unreacted nitrite is decomposed by the addition of urea and the reaction mixture is added to a solution of 1.8 parts of copper (I) chloride in 9 parts by volume of concentrated hydrochloric acid and 9 parts by volume of water. The reaction mixture is stirred at room temperature for 1 and half hours, stirred for a further 2 hours at 40° C. and is rendered alkaline to pH 10, diluted with ethyl acetate and filtered through hyflo. The organic layer is separated and the aqueous layer is extracted with 3×20 parts by volume of ethyl acetate. The combined organic fraction is dried over magnesium sulphate, filtered and concentrated under vacuum to give 6-(3-chlorophenyl-4-morpholino)-4,5-dihydro-5-methyl-3-(2H)-pyridazinone melting at 218°–221° C.

Calculated for $C_{15}H_{18}ClN_3O_2$; %C 58.53; %H 5.87; %N 13.66 Found: %C 58.40; %H 6.13; %N 13.76

EXAMPLE 7

6-(3-Cyanophenyl-4-morpholino)-4,5-dihydro-5-methyl-3(2H)-pyridazinone 5.0 parts of cupric sulphate in 20 parts by volume of water is added to a solution of 6.5 parts of potassium cyanide in 20 parts by volume of water at 60° C. The mixture is cooled to room temperature and added dropwise to a mixture of 2.2 parts 6-(3-amino-phenyl-4-morpholino}-4,5-dihydro-5-methyl-3(2H)-pyridazinone in 15 parts by volume of concentrated hydrochloric acid and 15 parts by volume of water diazotised at 0°–5° C. with a solution of 0.6 parts of sodium nitrite in 5 parts by volume of water and adjusted to pH 7.0 with dilute NaOH. The reaction mixture is stirred at room temperature for 2 hours, a further 2 hours at 80° C., cooled and filtered. The solid product was purified by chromatography on silica gel to give 6-(3-cyanophenyl-4-morpholino)-4,5-dihydro-5-methyl-3(2H)-pyridazinone melting at 223°–225° C.

Calculated for $C_{16}H_{18}N_4O_2$: %C 64.41; %H 6.08; %N 18.78 Found %C 64.33; %H 6.36; %N 18.56

EXAMPLE 8

6-(3-Cyano-4-morpholinoohenyl)-4,5-dihydro-5-ethyl-3(2H)-pyridazinone 10.5 g of 3-(3-cyano-4-morpholinobenzoyl)valeric acid, 2 ml of hydrazine hydrate and 100 ml of ethanol are stirred for 5 hours under reflux and then for 16 hours at room temperature. The reaction mixture is concentrated by evaporation and the residue is chromatographed over silica gel with an 8:2 mixture of toluene/ethyl acetate as eluant. After the separation 6-(3-cyano-4-morpholinophenyl)-4,5-dihydro-5-ethyl-3(2H)-pyridazinone is eluted. Melting point after recrystallisation from chloroform/diethyl ether: 217°–218° C.

The starting 3-(m-cyano-p-morpholinobenzoyl)valeric acid is prepared as follows:

4.9 ml of diisopropylamine and 10 g of 3-(3-cyano-4-morpholino-benzoyl)propionic acid are added to a suspension of 1.7 g of a 50% dispersion of sodium hydride in 35 ml of dimethylformamide and the mixture is heated for 5 minutes to reflux temperature. Then 28.9 ml of a 1.2 molar solution of butyllithium in hexane are added dropwise at −70° . The reaction mixture is stirred for a further 10 minutes at −30° and then 2.8 ml of ethyl iodide are added at −70° . The batch is stirred for a further 20 hours at room temperature with the addition of another 5.6 ml of ethyl iodide after the first 3 hours. For working up, water is added and the pH is adjusted to 1 with 120 ml of 1N hydrochloric acid. The aqueous phase is extracted with ether and the ethereal extracts are extracted with 2N sodium carbonate solution. The sodium carbonate extracts are in turn adjusted to pH 1 and then extracted with a 1:1 mixture of ether/ethyl acetate. These extracts are washed with brine, dried over sodium sulfate and concentrated by evaporation, affording 10.5 g of crude 3-(3-cyano-4-morpholinobenzoyl)valeric acid, which is further reacted direct as described above.

What is claimed is:

1. Pyridazinones of the general formula I

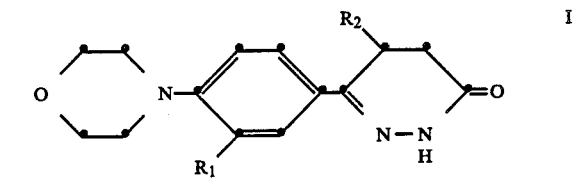

in which $R_1$ is cyano, and $R_2$ is $C_1$–$C_4$ alkyl; the tautomeric forms and salts thereof, as their racemic mixtures or as the individual optically-active forms.

2. Compounds of formula I given in claim 1 wherein $R_2$ is methyl or ethyl and $R_1$ has the meanings given in claim 1 and tautomeric forms, salts and optical isomers thereof.

3. Compounds of formula I given in claim 1 wherein $R_2$ is methyl and $R_1$ has the meanings given in claim 1 and tautomeric forms, salts and optical isomers thereof.

4. A compound of the general formula I according to claim 1 being 6-(3-cyanophenyl-4-morpholino)-4,5-dihydro-5-methyl-3-(2H)-pyridazinone, and the tautomeric form thereof.

5. Pharmaceutical composition for the treatment of thrombotic diseases comprising an effective amount of an antithrombotically-active compound of formula I as claimed in claim 1, together with a pharmaceutically-acceptable excipient.

* * * * *